United States Patent
Childress et al.

(10) Patent No.: US 10,301,806 B2
(45) Date of Patent: May 28, 2019

(54) DISINFECTION SYSTEMS AND METHODS FOR OPERATING A LIGHT SYSTEM

(71) Applicant: The Boeing Company, Chicago, IL (US)

(72) Inventors: Jamie J. Childress, Seattle, WA (US); Karen L. Hills, Seattle, WA (US); Melanie L. Kimsey-Lin, Seattle, WA (US); Claudia E. Fritz-Thompson, Bothell, WA (US)

(73) Assignee: The Boeing Company, Chicago, IL (US)

( * ) Notice: Subject to any disclaimer, the term of this patent is extended or adjusted under 35 U.S.C. 154(b) by 31 days.

(21) Appl. No.: 15/633,028

(22) Filed: Jun. 26, 2017

(65) Prior Publication Data
US 2018/0371733 A1    Dec. 27, 2018

(51) Int. Cl.
*E03D 9/00* (2006.01)
*E03D 5/10* (2006.01)
*B64D 11/02* (2006.01)
*A61L 2/10* (2006.01)

(52) U.S. Cl.
CPC .......... *E03D 9/00* (2013.01); *A61L 2/10* (2013.01); *B64D 11/02* (2013.01); *E03D 5/10* (2013.01); *A61L 2202/14* (2013.01)

(58) Field of Classification Search
USPC ............................................................ 4/222
See application file for complete search history.

(56) References Cited

U.S. PATENT DOCUMENTS

| | | |
|---|---|---|
| 5,483,127 A | 1/1996 | Widmayer |
| 9,623,133 B2 | 4/2017 | Childress et al. |
| 9,700,072 B2 | 7/2017 | Dobrinsky et al. |
| 9,783,974 B1 | 10/2017 | Tillotson |
| 2010/0193629 A1 | 8/2010 | Breit et al. |
| 2013/0330235 A1 | 12/2013 | Stibich et al. |
| 2016/0195427 A1 | 7/2016 | Vance et al. |
| 2016/0220716 A1* | 8/2016 | Childress .................. A61L 2/24 |
| 2016/0250362 A1 | 9/2016 | Mackin |
| 2017/0107659 A1 | 4/2017 | Hills |

(Continued)

OTHER PUBLICATIONS

Co-pending U.S. Appl. No. 15/237,710, filed Aug. 16, 2016.

(Continued)

*Primary Examiner* — Lauren A Crane
(74) *Attorney, Agent, or Firm* — McDonnell Boehnen Hulbert & Berghoff LLP (57) ABSTRACT

In an example, a system for disinfecting a lavatory in a vehicle includes a UV light source in the lavatory and configured to emit UV light when activated. The system also includes a switch actuatable between a first state and a second state. The switch is configured to: (i) while in the first state, provide an input power from a power source of the vehicle to a lavatory device in the lavatory, and (ii) while in the second state, provide the input power from the power source to the UV light source and cease providing the input power to the lavatory device. The system further includes an activation control system configured to actuate the switch between the first state and the second state to deactivate and activate the UV light source, respectively. The input power is insufficient to simultaneously operate the lavatory device and activate the UV light source.

20 Claims, 7 Drawing Sheets

(56) References Cited

U.S. PATENT DOCUMENTS

2017/0283062 A1 10/2017 Childress
2017/0283092 A1 10/2017 Brown et al.
2017/0284076 A1 10/2017 Jensen

OTHER PUBLICATIONS

Co-pending U.S. Appl. No. 15/241,438, filed Aug. 19, 2016.
Co-pending U.S. Appl. No. 15/245,251, filed Aug. 24, 2016.
Co-pending U.S. Appl. No. 15/259,685, filed Sep. 8, 2016.
Co-pending U.S. Appl. No. 15/271,349, filed Sep. 21, 2016.
Co-pending U.S. Appl. No. 15/273,814, filed Sep. 23, 2016.
Co-pending U.S. Appl. No. 15/632,968, filed Jun. 26, 2017.
Co-pending U.S. Appl. No. 15/633,085, filed Jun. 26, 2017.
Co-pending U.S. Appl. No. 15/633,121, filed Jun. 26, 2017.
Co-pending U.S. Appl. No. 15/633,142, filed Jun. 26, 2017.

* cited by examiner

DISINFECTION SYSTEMS AND METHODS FOR OPERATING A LIGHT SYSTEM

FIELD

The present disclosure generally relates to systems and methods for light systems, and more particularly to systems and methods for operating an ultraviolet (UV) light source to disinfect an environment.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using a UV light source.

SUMMARY

In an example, a system for disinfecting at least a portion of a lavatory in a vehicle is described. The system includes a UV light source in the lavatory and configured to emit UV light when activated, and a switch actuatable between a first state and a second state. The switch is configured to: (i) while in the first state, provide an input power from a power source of the vehicle to a lavatory device in the lavatory, and (ii) while in the second state, provide the input power from the power source to the UV light source and cease providing the input power to the lavatory device. The system also includes an activation control system configured to actuate the switch between the first state and the second state to deactivate and activate the UV light source, respectively. The input power is insufficient to simultaneously operate the lavatory device and activate the UV light source.

In another example, a method of operating a UV light source for a vehicle is described. The method includes receiving, at a lavatory of a vehicle, an input power from a power source of the vehicle. The method also includes providing, via a switch in a first state, the input power to a lavatory device. The method further includes operating, using the input power while the switch is in the first state, the lavatory device. Additionally, the method includes receiving, by the switch, a control signal from an activation control system. The method also includes, responsive to the control signal, switching the switch from the first state to a second state to: (i) provide the input power to the UV light source and (ii) cease providing the input power to the lavatory device. The method further includes activating, using the input power while the switch is in the second state, the UV light source to emit UV light in the lavatory.

In another example, a lavatory module configured to be installed in a vehicle is described. The lavatory module includes a plurality of walls and a door defining an interior space of the lavatory module, a toilet in the interior space, and a lavatory device configured to flush the toilet. The lavatory module also includes a UV light source configured to emit UV light in the interior space. The lavatory module further includes an input configured to receive an input power from an electrical distribution system of the vehicle and a switch coupled to the input and actuatable between: (i) a first state in which the switch provides the input power to the lavatory device, and (ii) a second state in which the switch provides the input power to the UV light source and ceases providing the input power to the lavatory device. The lavatory module also includes an activation control system configured to actuate the switch between the first state and the second state to deactivate and activate the UV light source, respectively. The input power is insufficient to simultaneously power the lavatory device and activate the UV light source.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

The systems and methods of the present disclosure provide disinfection systems for a vehicle and methods for operating a UV light source for a lavatory of a vehicle. When activated during an activation cycle, the UV light source emits UV light, which can kill and/or disable microorganisms such as bacteria, viruses, molds, and/or other pathogens. For example, when microorganisms are exposed to a sufficiently high dose of UV light, the UV light can damage nucleic acids and/or disrupt the deoxyribonucleic acid (DNA) of the microorganisms, rendering the microorganisms unable to carry out cellular functions and infect people.

The antimicrobial efficacy of the UV light during the activation cycle is related to factors such as, for instance, the length of time a microorganism is exposed to the UV light (i.e., the "exposure time"), the intensity of the UV light, and the wavelength of the UV light. As one example, the antimicrobial efficacy of the UV light at a particular wavelength can be specified as a UV dose, which can be determined based on an equation having the general form of:

$$\text{UV dose} = \text{UV light intensity} \times \text{exposure time} \quad \text{(eq. 1)}$$

where the UV dose is specified in mWs/cm$^2$, the UV light intensity is specified in mW/cm$^2$ at a predetermined distance (e.g., one meter) from the UV light source, and the exposure time is specified in seconds.

In general, the UV light source receives power from a power source of the vehicle and converts the power into the UV light. The power source may also provide power to other commodity systems of the vehicle. For example, an aircraft can have a power source that also provides power to, among other commodity systems, one or more motor flight control systems, electronic engine control systems, communication systems, navigation systems, cabin lighting systems, closet lighting systems, passenger service unit systems, audio visual systems, lavatory systems, and/or galley systems. To meet the power requirements of the various commodity systems, the vehicle can include an electrical distribution system that provides specific portions of the power supplied by the power source to the commodity systems in accordance with a power budget.

A challenge is presented when a lavatory of a vehicle is to be retrofitted with the UV light source as the power requirements of the UV light source may not have been taken into consideration when the power budget and electrical distribution system were designed. For example, based on the power budget, the power source and the electrical distribution system may provide a power to the lavatory that is insufficient to simultaneously operate electrical devices in the lavatory ("lavatory devices" such as, e.g., a water heater, a flush motor, and/or a vacuum blower) and activate the UV light source.

One approach to providing the UV light source with sufficient power is to run an additional power feeder (e.g., a conductor) from the power source to the UV light source in the lavatory. However, in some vehicles, the distance between the power source and the lavatory can be relatively long, and thus it may be costly and/or difficult to install the additional power feeder. For instance, on an aircraft, the additional power feeder may need to be run from an electrical equipment bay at a fore position of the aircraft (e.g., at the flight deck of the aircraft) to a lavatory at an aft position of the aircraft (e.g., at the aft-most portion of a passenger cabin). In such a scenario, the additional power feeder may have a length that is equal to or greater than approximately 100 feet (ft).

Similar challenges may also be encountered during an initial buildout of a new vehicle. For instance, providing an additional power feeder dedicated to the UV light source in the lavatory may be costly given that the UV light source may be operated relatively infrequently. Additionally, for instance, if the UV light source is specifically accounted for in the power budget as a separate system, the vehicle may require a power source with greater energy supply capabilities. This can lead to an increased size and/or weight of the power source, which may be undesirable in some implementations.

The disinfection systems and methods described herein can beneficially overcome challenges to operating the UV light source in a lavatory of a vehicle. Within examples, the disinfection systems and methods of the present disclosure include a UV light source, a switch, and an activation control system. The switch is actuatable between (i) a first state in which the switch couples the lavatory devices to an input power provided by a power source and decouples the UV light source from the input power, and (ii) a second state in which the switch couples the UV light source to the input power and decouples the lavatory devices from the input power. The activation control system can actuate the switch between the first state and the second state to deactivate and activate the UV light source, respectively.

Within examples, the input power may be insufficient to simultaneously operate the lavatory devices and activate the UV light source. However, the disinfection system can beneficially overcome this problem by actuating the switch to selectively couple either i) the UV light source or (ii) the lavatory devices to the input power at one time. By coupling the lavatory devices and decoupling the UV light source when the switch is in the first state, the input power is sufficient for operating the lavatory devices. Similarly, by coupling the UV light source and decoupling the lavatory devices, the input power is sufficient for activating the UV light source to emit UV light in the lavatory.

Figure 1:
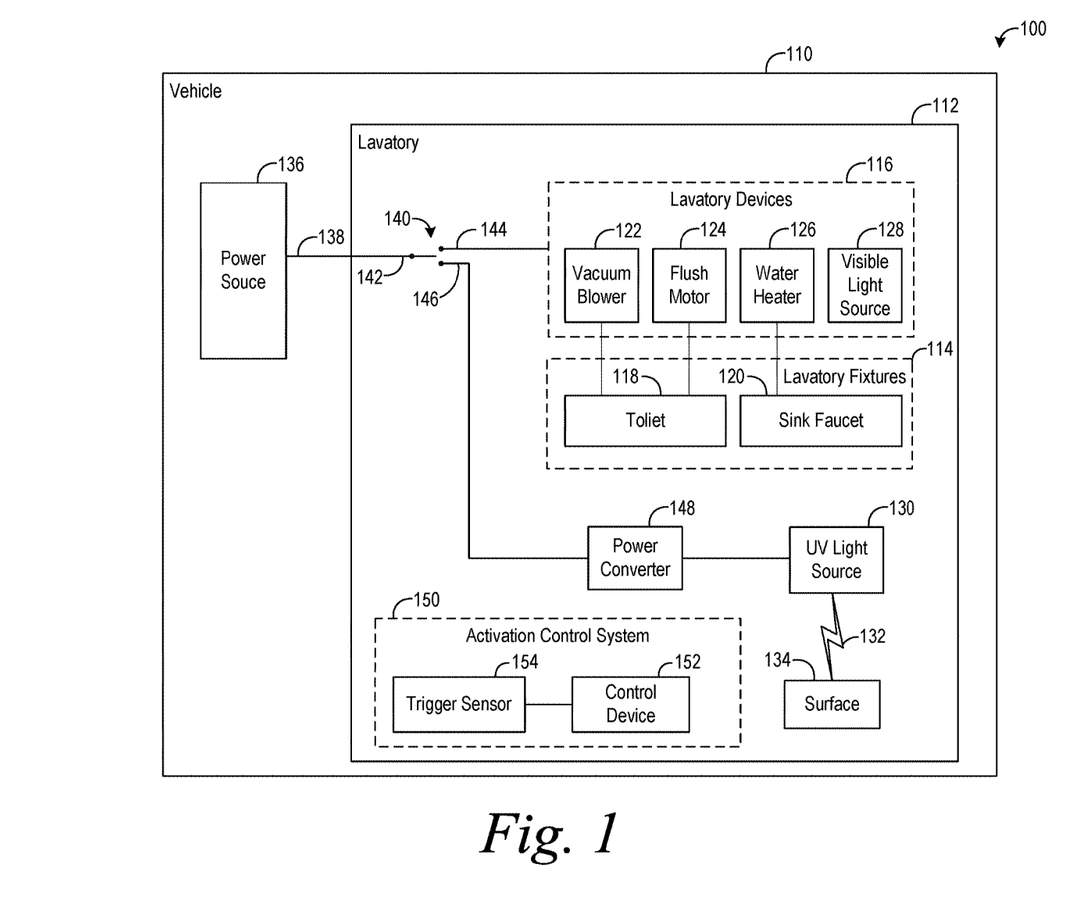
FIG. 1 illustrates a simplified block diagram of a disinfection system according to an example embodiment.

Referring now to FIG. 1, a disinfection system 100 for a vehicle 110 is depicted according to an example embodiment. The vehicle 110 can be an aircraft, an automobile (e.g., a car, a truck, a bus, and/or a van), a railed vehicle (e.g., a train and/or a tram), a watercraft (e.g., a ship and/or a boat), and/or a spacecraft.

As shown in FIG. 1, the vehicle 110 includes a lavatory 112. The lavatory 112 can include one or more lavatory fixtures 114, and one or more lavatory devices 116. For example, in FIG. 1, the lavatory fixtures 114 include a toilet 118 and a sink faucet 120. The lavatory fixtures 114 can additionally or alternatively include other fixtures such as, for instance, a shower and/or a bathtub in additional or alternative examples.

The lavatory devices 116 are electrical devices of the lavatory 112 that are operated in the presence of people, to facilitate using the toilet 118, to facilitate using the sink faucet 120, and/or to facilitate operating a fan. As examples, in FIG. 1, the lavatory devices 116 include a vacuum blower 122, a flush motor 124, a water heater 126, and a visible light source 128. The vacuum blower 122 and the flush motor 124 can flush the toilet 118 in the lavatory 112. The water heater 126 can heat water that is provided at the sink faucet 120 in the lavatory 112 (e.g., to facilitate washing a person's hands). The visible light source 128 can emit visible light to facilitate a user seeing and operating the toilet 118 and/or the sink faucet 120. As further examples, the lavatory devices 116 can additionally or alternatively include a hand dryer (e.g., a blower), an automated soap dispenser, an automated towel dispenser, an automated toilet paper dispenser, and/or an automated toilet seat cover.

The lavatory 112 further includes a UV light source 130, which is separate and distinct from the lavatory devices 116. When activated, the UV light source 130 can emit UV light 132 to disinfect an environment in the lavatory 112. For instance, the environment that is disinfected by the UV light 132 can include a surface 134 in the lavatory 112 (e.g., a surface of the toilet 118, the sink faucet 120, a sink basin, and/or a counter in the lavatory 112).

As examples, the UV light source 130 can include one or more excimer bulbs, mercury-vapor lamps, downshifting phosphor lamps, and/or light emitting diodes (LEDs). More generally, the UV light source 130 can be a light source that emits the UV light 132 at a wavelength within the UV spectrum (i.e., between approximately 10 nanometers (nm) and approximately 400 nm). In some implementations, the UV light source 130 can be a light source that emits UV light 132 at a wavelength within the far-UV spectrum (e.g., between approximately 190 nm and approximately 240 nm). For instance, in one implementation, the UV light source 130 can be a light source that emits the UV light 132 at a wavelength of approximately 222 nm. By emitting the UV light 132 at a wavelength in the far-UV spectrum, the UV light source 130 can more rapidly disinfect the environment than by emitting the UV light 132 at other wavelengths in the UV spectrum.

Also, within examples, the UV light source 130 can emit the UV light 132 at a predetermined wavelength and intensity for a predetermined exposure time to achieve a target level of antimicrobial efficacy during an activation cycle. In one example, the UV light source 130 can emit the UV light 132 at an intensity of 1 mW/cm$^2$ for an exposure time of 10 seconds to achieve the target level of antimicrobial efficacy for the activation cycle (i.e., at a dose of approximately 1 mWs/cm$^2$). In additional or alternative examples, the target level of antimicrobial efficacy can be a UV dose between approximately 2 mWs/cm$^2$ and approximately 500 mWs/cm$^2$. Different microorganisms may have different abilities to withstand exposure to the UV light 132. In some implementations, the target level of antimicrobial efficacy can be based on a target microorganism-kill rate for one or more types of microorganisms that are targeted for disinfection by the disinfection system 100. As an example, the targeted microorganism kill rate can be approximately 80% to approximately 99.99%. For instance, the targeted microorganism-kill rate can be approximately 80%, approximately 90%, approximately 95%, approximately 99%, approximately 99.9%, and/or approximately 99.99% of the one or more target microorganisms irradiated by the UV dose.

Additionally, as shown in FIG. 1, the vehicle 110 includes a power source 136 that provides an input power to the lavatory 112 of the vehicle 110 via a power conductor 138. In one example, the power source 136 can provide the input power to the lavatory 112 as an alternating current (AC) power. For instance, the power source 136 can include an engine turbine that generates electrical energy during operation of the vehicle 110. Other example power sources 136 are also possible.

The lavatory devices 116 and the UV light source 130 can be selectively coupled to the power conductor 138 by a switch 140, which is actuatable between a first state and a second state. In general, the switch 140 is configured to: (i) while in the first state, provide the input power from the power source 136 of the vehicle 110 to the lavatory devices 116 in the lavatory 112, and (ii) while in the second state, provide the input power from the power source 136 to the UV light source 130 and cease providing the input power to the lavatory devices 116.

For example, in FIG. 1, the switch 140 is a single pole double throw switch having a common terminal 142 configured to receive the input power from the power source 136, a first terminal 144 coupled to the lavatory devices 116, and a second terminal 146 coupled to the UV light source 130. In this arrangement, the switch 140 couples the lavatory devices 116 to the power source 136 and decouples the UV light source 130 from the power source 136 when the switch 140 is in the first state. As such, when the switch 140 is in the first state, the lavatory devices 116 can use the input power to perform lavatory operations (e.g., flushing the toilet 118, heating water to be provided at the sink faucet 120, and/or illuminate the lavatory 112 with visible light). Whereas, the switch 140 couples the UV light source 130 to the power source 136 (e.g., via a power converter 148) and decouples the lavatory devices 116 from the power source 136 when the switch 140 is in the second state. Accordingly, when the switch 140 is in the second state, the UV light source 130 can use the input power to emit the UV light 132.

Although the switch 140 is a single throw double pole switch in FIG. 1, the switch 140 can additionally or alternatively include one or more single throw switches, single pole double throw switches, transistors, and/or diodes in other examples. For instance, another example in which the switch 140 includes two switches is described in further detail below with respect to FIG. 3.

Within examples, the input power may be insufficient to simultaneously operate the lavatory devices 116 and activate the UV light source 130. The switch 140 can beneficially overcome this problem by selectively coupling one of (i) the UV light source 130 or (ii) the lavatory devices 116 to the input power on the power conductor 138 at one time. By coupling the UV light source 130 and decoupling the lavatory devices 116, the input power is sufficient for activating the UV light source 130 to emit UV light 132 in the lavatory 112. Similarly, by coupling the lavatory devices 116 and decoupling the UV light source 130, the input power is sufficient for operating the lavatory devices 116.

For instance, in one example, the power conductor 138 can provide the input power at approximately 1 kW to approximately 1.25 kW based on a power budget for the vehicle 110. In this example, the lavatory devices 116 can use approximately 0.75 kW when operating at a peak loading condition, and the UV light source 130 can use approximately 1.0 kW to approximately 1.2 kW during an activation cycle to emit the UV light 132 at the target level of antimicrobial efficacy. Accordingly, in this example, the input power is approximately 0.75 kW in sufficient to simultaneously operate the lavatory devices 116 and activate the UV light source 130, but the input power is sufficient to separately operate the lavatory devices 116 or activate the UV light source 130 based on the state of the switch 140.

In some examples, the disinfection system 100 can further include a power converter 148 to condition the input power on the power conductor 138 for use by the UV light source 130. For instance, when the switch 140 is in the second state, the power converter 148 receives the input power. The power converter 148 converts the input power to a supply power and outputs the supply power to the UV light source 130. In an example, the supply power can have a different alternating current (AC) waveform than the input power. For instance, the power converter 148 can modify one or more of a frequency, a voltage, a current, and/or a wattage of the AC waveform of the input power to form the supply power. In this way, the power converter 148 can adapt the input power received from the power conductor 138 to efficiently operate the UV light source 130, for example, at a target level of antimicrobial efficacy (e.g., at an intensity and/or for an exposure time corresponding to the target level of antimicrobial efficacy). An example block diagram of the power converter 148 is described further below with respect to FIG. 2.

As shown in FIG. 1, the disinfection system 100 can also include an activation control system 150, which can control activating and deactivating the UV light source 130. For example, activation control system 150 can include a control device 152 in communication with one or more triggers sensors 154 and the UV light source 130 (and/or the power converter 148). The trigger sensor(s) 154 can detect one or more trigger conditions and responsively generate a sensor signal indicating that the trigger condition(s) were detected. The control device 152 can (i) receive the sensor signal indicating that the trigger condition was detected, (ii) determine, based on the sensor signal, that one or more criteria are met, and (iii) responsive to the determination that the one or more criteria are met, transmit a control signal to the switch 140, the UV light source 130, and/or the power converter 148 to activate the UV light source 130.

In an example, the trigger sensor(s) 154 can include a motion sensor, an occupancy sensor, a thermal sensor, an open/close sensor, an infrared sensor device, an ultrasonic sensor device, a floor pressure sensor, and/or other types of sensors. For instance, the trigger condition(s) detected by the trigger sensor(s) 154 can include a door of the lavatory 112 being opened, the door of the lavatory 112 being closed, the lavatory 112 being occupied, and/or the lavatory 112 being unoccupied. Additionally, for example, the one or more criteria that is used by the control device 152 to determine whether to activate the UV light source 130 can include one or more criterion such as a door of the lavatory 112 being closed, the lavatory 112 being unoccupied, the lavatory 112 having been occupied a predetermined number of times since a previous activation of the UV light source 130, and/or a predetermined amount of time having passed since the previous activation of the UV light source 130. As such, within examples, the activation control system 150 can activate the UV light source 130 when people are not present.

In one example, responsive to the control device 152 determining that the one or more criteria are met, the control device 152 transmits the control signal to the switch 140 to actuate the switch 140 from the first state to the second state. In one implantation, the input power is sufficient to immediately activate the UV light source 130 responsive to the switch 140 actuating to the second state. For instance, the UV light source 130 can draw 1 kW to emit the UV light 132 and the input power can have a wattage that is equal to or greater than 1 kW. After a predetermined exposure time has elapsed, the control device 152 can transmit a second control signal to the switch 140 to actuate the switch 140 from the second state to the first state. In this way, the control device 152 can deactivate and activate the UV light source 130 by actuating the switch 140 between the first state and the second state, respectively.

In other examples, the control device 152 can additionally or alternatively transmit the control signal to the UV light source 130 and/or the power converter 148 to activate and/or deactivate the UV light source 130. For instance, the control device 152 can transmit a first control signal to actuate the switch 140 and then transmit a second control signal to activate the UV light source 130. This may be beneficial in an example in which the power converter 148 includes a power buffer, which can be first charged using the input power before activating the UV light source 130.

In general, the control device 152 is a computing device that is configured to control operation of the disinfection system 100. As such, the control device 152 can be implemented using hardware, software, and/or firmware. For example, the control device 152 can include one or more processors and a non-transitory computer readable medium (e.g., volatile and/or non-volatile memory) that stores machine language instructions or other executable instructions. The instructions, when executed by the one or more processors, cause the disinfection system 100 to carry out the various operations described herein. The control device 152, thus, can receive data (including data indicated by the sensor signals) and store the data in memory as well.

Figure 2:
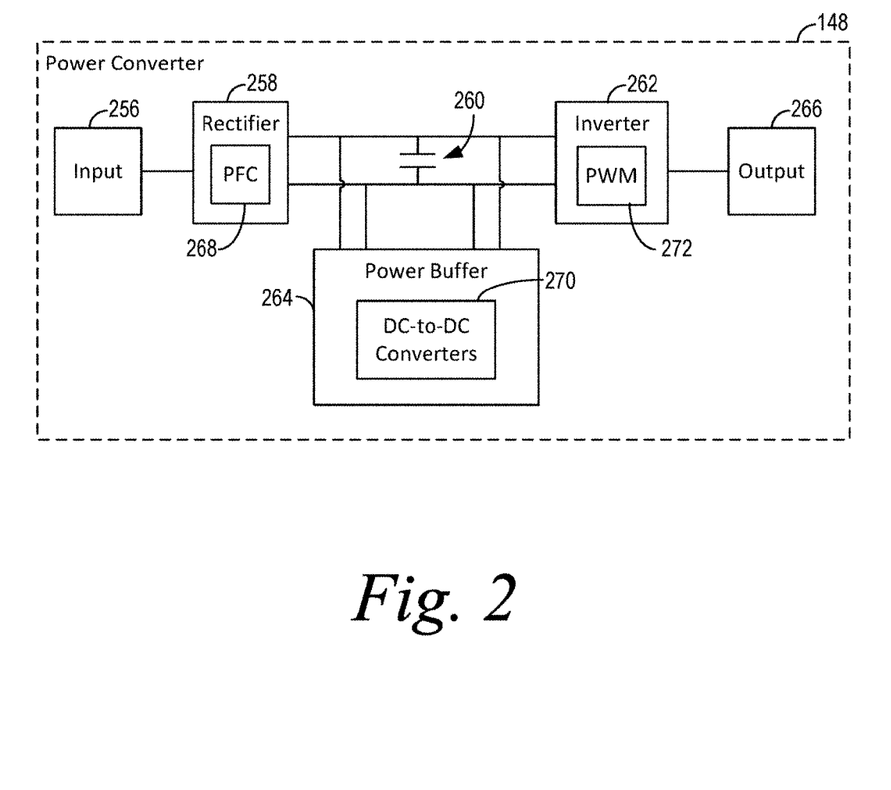
FIG. 2 illustrates a simplified block diagram of a power converter according to an example embodiment.

FIG. 2 depicts the power converter 148, including a power buffer 264, according to an example embodiment. As shown in FIG. 2, the power converter 148 includes the input 256, a rectifier 258, a direct current (DC) link 260, an inverter 262, the power buffer 264, and an output 266. The input 256 receives the input power from the power source 136. The rectifier 258 is coupled to and receives the input power from the input 256. The rectifier 258 can convert the AC input power into a DC power. In an example, the rectifier 258 includes a power factor corrector (PFC) 268 that corrects a power factor of the input power to facilitate more efficient use of the input power by the disinfection system 100. The PFC 268 can also facilitate isolating the power converter 148 and/or the UV light source 130 from the power source 136 (and/or other electrical subsystems coupled to the power source 136). Within examples, the PFC 268 can include a passive PFC circuit, an active PFC circuit, and/or a dynamic PFC circuit.

The rectifier 258 is coupled to the inverter 262 via the DC link 260. When the switch 140 is in the second state and the light source 130 is activated, the inverter 262 converts the DC power received from the rectifier 258 into an AC power, which provides a portion of the supply power at the output 266. The DC link 260 facilitates the coupling of the rectifier 258 and the inverter 262. In one example, the DC link 260 can include a capacitor coupled in parallel between the rectifier 258 and the inverter 262. The DC link 260 can assist in mitigating transients propagating toward the power source 136 and/or assist in smoothing pulses in the rectified DC power provided by the rectifier 258.

As shown in FIG. 2, the power buffer 264 is coupled in parallel between the rectifier 258 and the DC link 260, and between the DC link 260 and the inverter 262. The power buffer 264 stores power using the input power received at the input 256 when the switch 140 is in the second state and the UV light source 130 deactivated. As examples, the power buffer 264 can include a battery, a capacitor, and/or another type of energy storage device.

In the example of FIG. 2, the power buffer 264 includes a plurality of DC-to-DC converters 270 coupled to each other. When the UV light source 130 is deactivated, the DC-to-DC converters 270 receive the DC power from the rectifier 258. In one implementation, the DC-to-DC converters 270 include a first DC-to-DC converter that steps down the DC power received from the rectifier 258 and a second DC-to-DC converter that steps up the DC power. This configuration of the DC-to-DC converters 270 can beneficially reduce (or minimize) the size and/or weight of the power buffer 264.

As noted above, the inverter 262 is coupled to the rectifier 258 and the power buffer 264. In this arrangement, when the switch 140 is in the second state and the light source 130 is activated, the inverter 262 can receive the DC power from the rectifier 258 and the power stored in the power buffer 264. The inverter 262 can convert this combination of DC power from the rectifier 258 and the power buffer 264 into the supply power, which has an AC waveform. In an example, the inverter 262 can include a pulse-width modulator (PWM) 272, which can switch on and off to control a frequency and/or wattage of the supply power. In another example, the inverter 262 can additionally or alternatively include a sine wave generator and/or a carrier wave generator to convert the combination of DC power to the supply power.

The power converter 148 depicted in FIG. 2 can facilitate activating the UV light source 130 in an scenario in which the input power has a low wattage relative to a power requirement of the UV light source 130. For example, when the switch 140 is in the second state, the power converter 148 can receive the input power from the power source 136 during a first portion of a time interval and a second portion of the time interval. The UV light source 130 is deactivated during the first portion of the time interval. The UV light source 130 is activated during the second portion of the time interval (e.g., responsive to the second control signal transmitted by the control device 152 in FIG. 1). However, the input power received during the second portion of the time interval is insufficient by itself for the UV light source 130 to emit the UV light 132 at the intensity providing the target level of antimicrobial efficacy for a given activation cycle.

To address this limitation of the input power, the power converter 148 can store the input power in the power buffer 264 during the first portion of the time interval. Later, during the second portion of the time interval, the power converter 148 can provide to the UV light source 130 the supply power that combines (i) the input power received at the input 256 during the second portion of the time interval and (ii) the power stored in the power buffer 264 during the first portion of the time interval. The combination of power is sufficient for activating the UV light source 130 to emit the UV light 132 at the target level of antimicrobial efficacy.

In one example, the target level of antimicrobial efficacy can be defined by an intensity of 1 mW/cm$^2$ intensity and an exposure time of 10 seconds. In this example, when the switch 140 is in the second state, the input 256 receives the input power as a three-phase AC power with a voltage of approximately 115 $V_{AC}$, a frequency of approximately 360 Hz to approximately 800 Hz, and a current of 0.5 Amps (A) such that the input power has a wattage of approximately 100 W (i.e., less than 1 kW). As such, the input power is insufficient by itself to activate the UV light source 130 at the target level of antimicrobial efficacy. The rectifier 258 can convert the input power to the DC power having a voltage of approximately 200 $V_{DC}$ and a current of approximately 0.5 A. The power buffer 264 can include a first DC-to-DC converter that steps down the DC power from 200 $V_{DC}$ to 28 $V_{DC}$, and a second DC-to-DC converter that steps the DC power from 28 $V_{DC}$ to 200 $V_{DC}$.

In this arrangement, during the first portion of the time interval, the rectifier 258 converts the input power to the 200 $V_{DC}$ power and the power buffer 264 stores the 200 $V_{DC}$ power. During the second portion of the time interval, the rectifier 258 converts the input power to the 200 $V_{DC}$ power and provides the 200 $V_{DC}$ power to the inverter 262. Also, during the second portion of the time interval, the power buffer 264 provides the stored power to the inverter 262 with a voltage of approximately 200 $V_{DC}$ and a current of approximately 5 A. As a result, the inverter 262 receives the combination of power at 200 $V_{DC}$ and a current of at least 5 A such that the supply power has a wattage equal to or greater than 1 kW. In this example, the power buffer 264 can have an energy storage capacity at least large enough to provide the stored power at 200 $V_{DC}$ and 5 A for the 10 second exposure time. In this way, the power converter 148 can provide the UV light source 130 with sufficient power to achieve the target level of antimicrobial efficacy during the activation cycle of the UV light source 130 and while the switch 140 is in the second state.

In the example described above, the power stored in the power buffer 264 provides approximately 90% of the supply power and the input power received during the second portion of the time interval provides approximately 10% of the supply power. In additional or alternative examples, the input power received during the second portion of time can provide approximately 5% to approximately 95% of the supply power and the power stored in the power buffer 264 can provide the remainder of the supply power.

Although the power converter 148 can beneficially overcome challenges to operating the UV light source 130 at the target level of antimicrobial efficacy in a limited-power environment, the power converter 148 can omit the power buffer 264 in alternative examples in which the input power is not limited relative to the power requirements of the UV light source 130. Omitting the power buffer 264 can beneficially further reduce the weight and/or size of the power converter 148.

Figure 3:
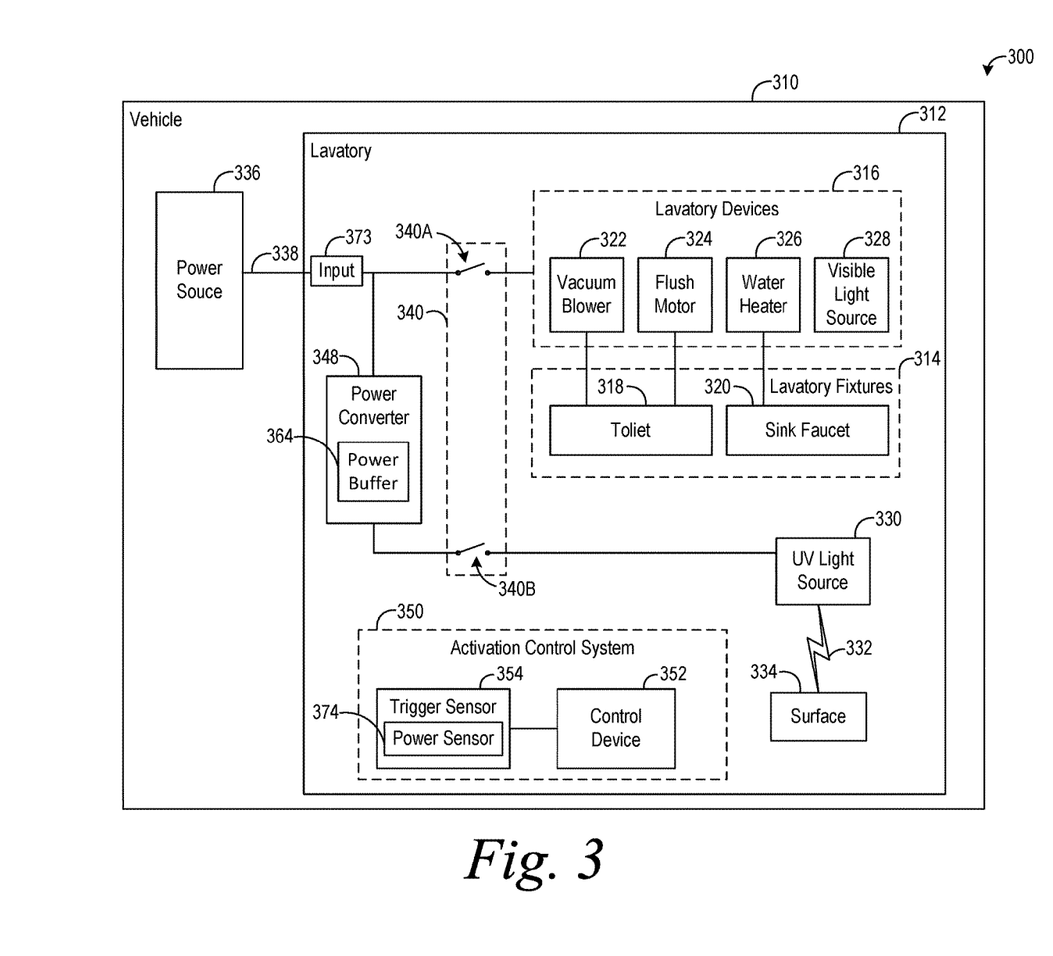
FIG. 3 illustrates a simplified block diagram of a disinfection system according to another example embodiment.

As noted above, in alternative examples, the switch 140 can have a different configuration than the single pole double throw switch depicted in FIG. 1. FIG. 3 depicts a disinfection system 300 according to another example embodiment. As shown in FIG. 3, the disinfection system 300 can be substantially the same as the disinfection system 100 described above with respect to FIG. 1. Accordingly, the disinfection system 300 can include a vehicle 310, a lavatory 312, lavatory fixtures 314, lavatory devices 316, a toilet 318, a sink faucet 320, a vacuum blower 322, a flush motor 324, a water heater 326, a visible light source 328, a UV light source 330 that can emit UV light 332, a surface 334, a power source 336, a power conductor 338, a switch 340, a power converter 348, an activation control system 350, a control device 352, and a trigger sensor 354 as described above.

In FIG. 3, the power converter 348 includes a power buffer 364. For instance, the power converter 348 can be configured as described above with respect to FIG. 2. As described above, the power converter 348 can receive the input power from the power source 336 (via the power conductor 338) and convert the input power to the supply power. Accordingly, the power buffer 364 is configured to store power, and the supply power can include a combination of the power stored in the power buffer 364 and the input power provided by the switch 340 while in the second state. Also, in FIG. 3, an input 373 is coupled to the power converter 348 and configured to receive the input power from the power source 336 (via the power conductor 338).

In FIG. 3, however, the switch 340 includes a first switch 340A and a second switch 340B. The first switch 340A can selectively couple the lavatory devices 316 to the input 373, and the second switch 340B can selectively couple the UV light source 330 to the power converter 348. In the first state of the switch 340, the first switch 340A is closed and the second switch 340B is open such that the lavatory devices 316 receives a first portion of the input power, the power buffer 364 receives a second portion of the input power, and the UV light source 330 is decoupled from the input power. In the second state of the switch 340, the first switch 340A is open and the second switch 340B is closed such that the lavatory devices 316 are decoupled from the input power and the UV light source 330 receives, via the supply power provided by the power converter 348, the input power. In this arrangement, the power buffer 364 can receive and store the input power when the switch 340 is in the first state so that the UV light source 330 can be more rapidly activated when the switch 340 is actuated to the second state.

Additionally, as shown in FIG. 3, the trigger sensor(s) 354 can include a power sensor 374 configured to determine an amount of power stored in the power buffer 364. For example, the power sensor 374 can include a voltmeter that can measure the amount of power stored in the power buffer 364. The power sensor 374 can also transmit to the control device 352 the sensor signal to indicate the amount of power stored in the power buffer 364.

In one example, the control device 352 can determine whether the indicated amount of power is sufficient to activate the UV light source 330. For instance, the control device 352 can compare the determined amount of power indicated by the sensor signal to a threshold amount of power stored in the control device 352. Responsive to the control device 352 determining that the determined amount of power is greater than the threshold amount of power, the control device 352 can transmit the control signal to the UV light source 330 and/or the power converter 348 to activate the UV light source 330. Whereas, responsive to the control device 352 determining that the determined amount of power is less than the threshold amount of power, the control device 352 can continue to wait until the power buffer 364 has at least the threshold amount of power before transmitting the control signal.

As such, the activation control system 350 can adjust, based on the determined amount of power stored in the power buffer 364, a parameter for activating the UV light source 330 during an activation cycle. For instance, in the example described above, the parameter can include a time for initiating the activation cycle. In an additional or alternative example, the parameter can include a duration of the activation cycle during which the UV light source 330 emits the UV light 332 (i.e., the exposure time). For instance, the control device 352 can store a table including a plurality of amounts of power and a plurality of durations. Each amount of table can correspond to a respective one of the durations in the table. As such, in this implementation, the control device 352 can use the determined amount of power indicated by the sensor signal to lookup the corresponding duration in the table, and then activate the UV light source 330 for the duration.

Figure 4:
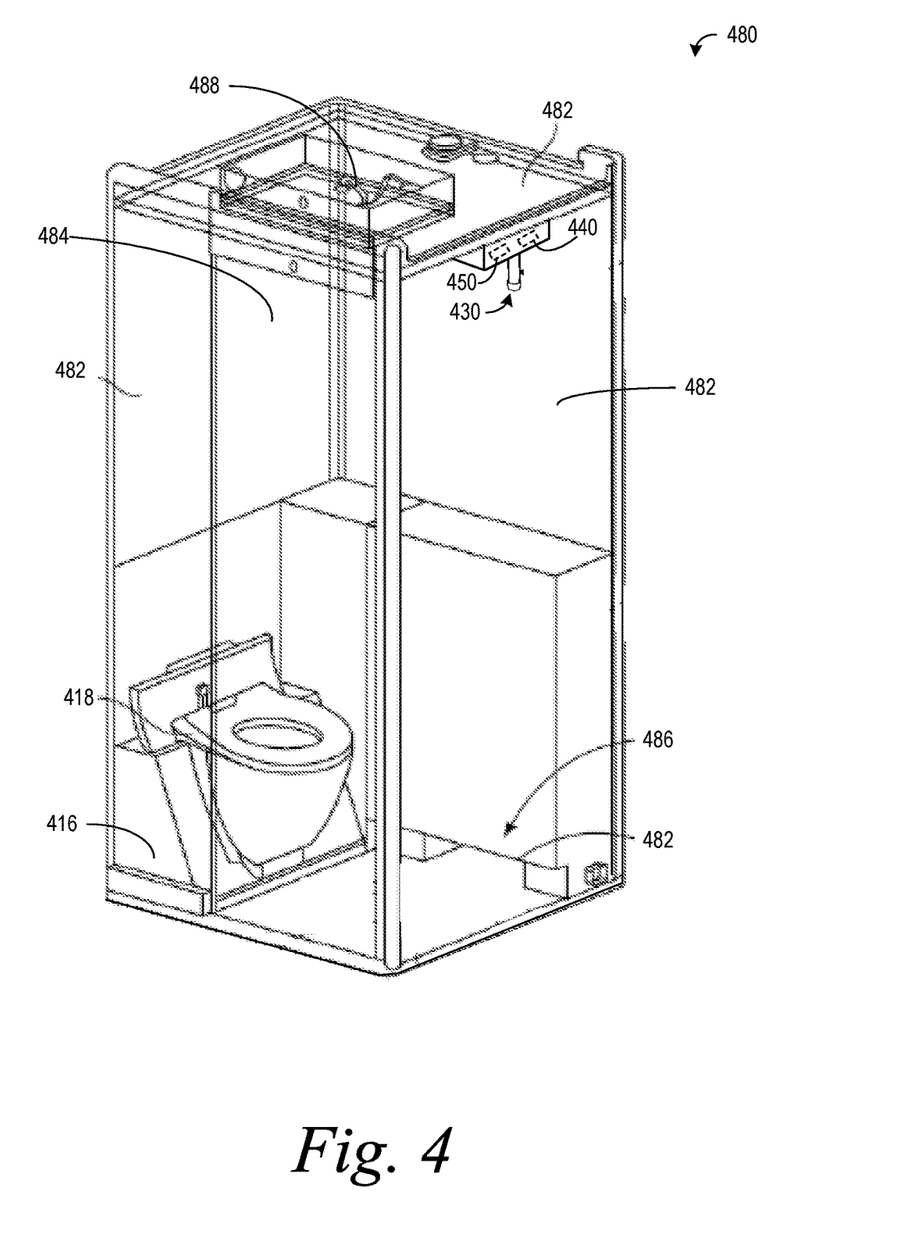
FIG. 4 illustrates a perspective view of a lavatory module according to an example embodiment.

Referring now to FIG. 4, a lavatory module 480 is depicted according to an example embodiment. As shown in FIG. 4, the lavatory module 480 includes a plurality of walls 482 and a door 484 defining an interior space 486 of the lavatory module 480. The lavatory module 480 also includes a toilet 418 in the interior space 486 and a lavatory device 416 configured to flush the toilet 418. For instance, the lavatory device 416 can include a vacuum blower and/or a flush motor, as described above.

Additionally, as shown in FIG. 4, the lavatory module 480 includes a UV light source 430 configured to emit UV light in the interior space 486. In FIG. 4, the UV light source 430 is at an elevated position in the interior space 486 (e.g., on a topmost one of the walls 482) of the lavatory module 480. Positioning the UV light source 430 at an elevated position can facilitate the UV light source 430 irradiating a greater surface area in the lavatory module 480; however, the UV light source 430 can be at a different position in the interior space 486 in additional or alternative examples.

The lavatory module 480 includes an input 488 configured to receive the input power from an electrical distribution system of the vehicle (e.g., the power conductor 138, 338 of the vehicle 110, 310 described above with respect to FIGS. 1 and 3). Additionally, the lavatory module 480 includes a housing 490 enclosing one or more components of a disinfection system (e.g., the disinfection systems 100 and 300 described above). For instance, in FIG. 4, the housing 490 includes a switch 440 coupled to the input 488 and actuatable between: (i) a first state in which the switch 440 provides the input power to the lavatory device 416, and (ii) a second state in which the switch 440 provides the input power to the UV light source 430 and ceases providing the input power to the lavatory device 416 as described above. Also, in FIG. 4, the housing 490 includes an activation control system 450 configured to actuate the switch 440 between the first state and the second state to deactivate and activate the UV light source 430, respectively.

The housing 490 can include additional or alternative components of the disinfection systems 100, 300 described herein. For instance, the housing 490 can additionally or alternatively include a power converter (e.g., the power converters 148, 348). Further, in additional or alternative examples, one or more of the components of the disinfection systems 100, 300 can be in additional or alternative housings in one or more additional or alternative locations in the lavatory module 480.

Within examples, the lavatory module 480 can be pre-assembled and then installed in the vehicle 110, 310 as a unit. This can provide for efficient manufacture, assembly, and/or installation of the lavatory module 480 in the vehicle 110, 310. For instance, after the lavatory module 480 is pre-assembled, the lavatory module 480 can be placed in the vehicle 110, 310. Once placed in the vehicle 110, 310, the input 488 can be coupled to the electrical distribution system of the vehicle 110, 310 (e.g., the power conductor 138, 338).

In operation, the lavatory 112, 312 and/or the lavatory module 480 of the vehicle 110, 310 can receive the input power from the power source 136, 336. The switch 140, 340 can initially be in the first state. While the switch 140, 340, 440 is in the first state, the switch 140, 340, 440 can provide the input power from the power source 136, 336 to the lavatory device(s) 116, 316, 416. The lavatory device(s) 116, 316, 416 can use the input power to perform operations such as, for example, heating water using the water heater 126, 326, operating the flush motor 124, 324 to flush the toilet 118, 318, 418 and/or operating the vacuum blower 122, 322 to flush the toilet 118, 318, 418.

In some examples, the switch 340 can also provide a portion of the input power to the power buffer 364 while in the first state (e.g., as shown in FIG. 3). In such examples, the power buffer 364 can store the portion of the input power for later use during an activation cycle. Whereas, in other examples, the switch 140 can decouple the power buffer 164 and the UV light source 130 from the input power while in the first state (e.g., as shown in FIG. 1).

The activation control system 150, 350, 450 can initiate the activation cycle of the UV light source 130, 330, 430. For instance, the trigger sensor(s) 154, 354 can detect the trigger condition and transmit a sensor signal to the control device 152, 352 indicating that the trigger condition was detected. The control device 152, 352 can determine, based on the sensor signal, that the one or more criteria are met and responsively provide the control signal to the switch 140, 340, 440.

The switch 140, 340, 440 can receive the control signal from the activation control system 150, 350, 450 and responsively switch from the first state to the second state to: (i) provide the input power to the UV light source 130, 330, 430 and (ii) cease providing the input power to the lavatory device(s) 116, 316, 416. For instance, the power converter 148, 348 can provide the input power to UV light source 130, 330, 430 via the supply power. In this way, the UV light source 130, 330, 430 can use the input power to emit the UV light 132, 332 in the lavatory 112, 312 and/or the lavatory module 480.

In some examples, prior to activating the UV light source 130, 330, 430, the power sensor 374 can determine the amount of power stored in the power buffer 364 and transmit the sensor signal to the control device 352 indicating the determined amount of power. Based on the determined amount of power stored in the power buffer 364, the control device 352 can adjust the parameter for activing the UV light source 330. For instance, the control device 352 can adjust the time for activating the UV light source 330 and/or the duration for which the UV light source 330 is activated. In this way, the activation control system 350 can adjust, based on the determined amount of power stored in the power buffer 364, a parameter for activating the UV light source 330 during an activation cycle.

Once the activation cycle is completed, the activation control system 150, 350, 450 can transmit another control signal to actuate the switch 140, 340, 440 from the first state to the second state. The process may then be repeated.

Figure 5:
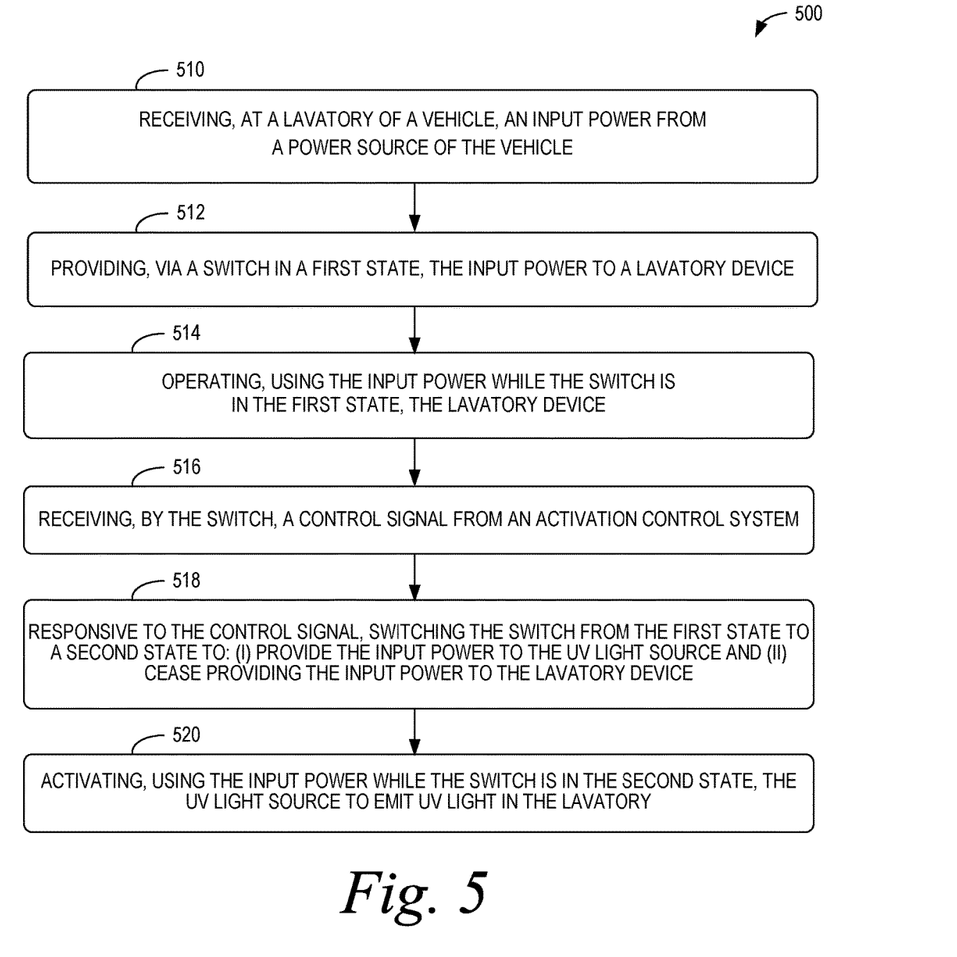
FIG. 5 illustrates a flow chart of an example process for operating a UV light source according to an example embodiment.

Referring now to FIG. 5, a flowchart for a process 500 of operating a UV light source for a vehicle is illustrated according to an example embodiment. As shown in FIG. 5, at block 510, the process 500 includes receiving, at a lavatory of a vehicle, an input power from a power source of the vehicle. At block 512, the process 500 includes providing, via a switch in a first state, the input power to a lavatory device. At block 514, the process 500 includes operating, using the input power while the switch is in the first state, the lavatory device. At block 516, the process 500 includes receiving, by the switch, a control signal from an activation control system. At block 518, the process 500 includes, responsive to the control signal, switching the switch from the first state to a second state to: (i) provide the input power to the UV light source and (ii) cease providing the input power to the lavatory device. At block 520, the process 500 includes activating, using the input power while the switch is in the second state, the UV light source to emit UV light in the lavatory.

Figure 6:
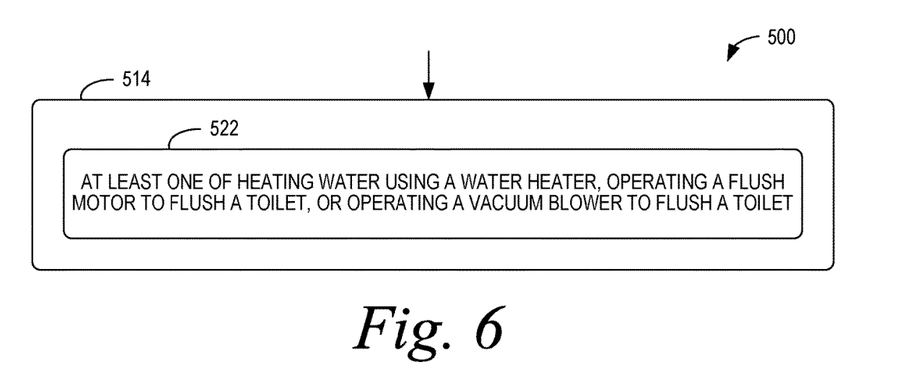
FIG. 6 illustrates a flow chart of an example process for operating a UV light source that can be used with the process shown in FIG. 5.

FIGS. 6-9 depict additional aspects of the process 500 according to further examples. As shown in FIG. 6, operating the lavatory device at block 514 can include at least one of heating water using a water heater, operating a flush motor to flush a toilet, or operating a vacuum blower to flush a toilet at block 522.

Figure 7:
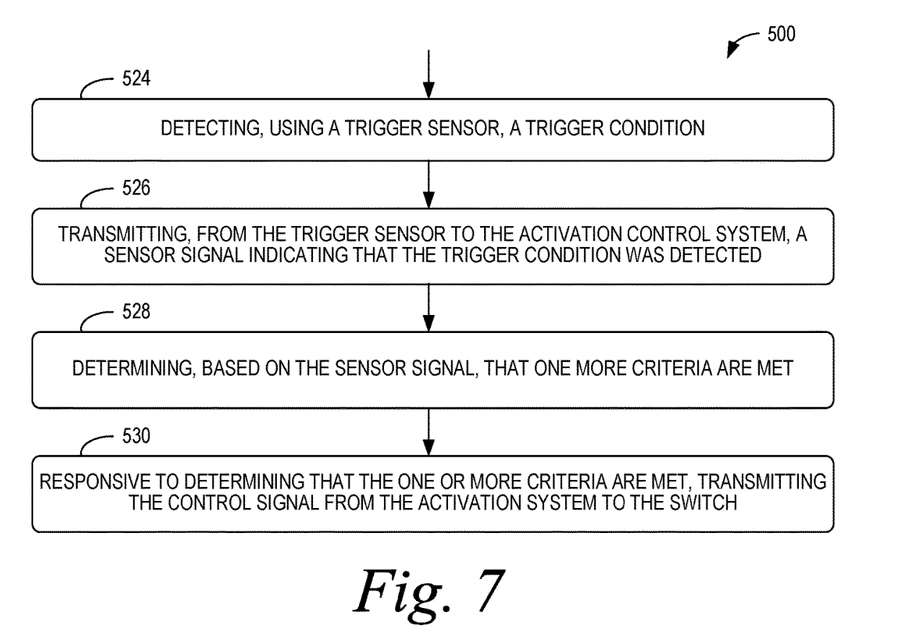
FIG. 7 illustrates a flow chart of an example process for operating a UV light source that can be used with the process shown in FIGS. 5-6.

As shown in FIG. 7, the process 500 can also include detecting, using a sensor, a trigger condition at block 524. At block 526, the process 500 can include transmitting, from the sensor to the activation control system, a sensor signal indicating that the trigger condition was detected. At block 528, the process 500 can include determining, based on the sensor signal, that one more criteria are met. At block 530, the process 500 can include, responsive to determining that the one or more criteria are met at block 528, transmitting the control signal from the activation system to the switch.

Figure 8:
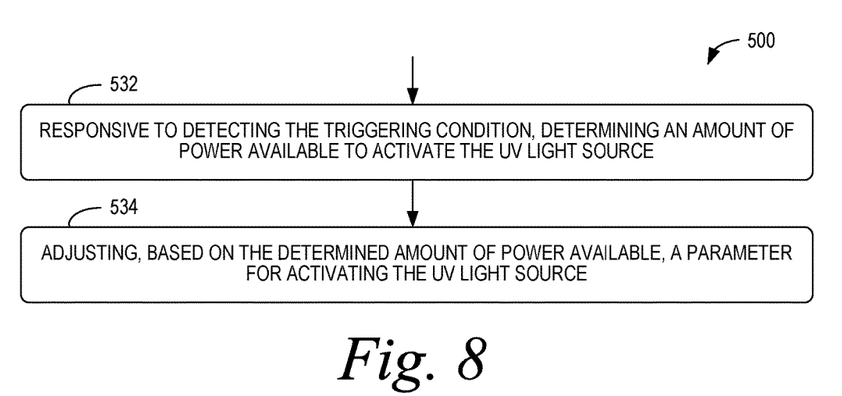
FIG. 8 illustrates a flow chart of an example process for operating a UV light source that can be used with the process shown in FIGS. 5-7.

As shown in FIG. 8, the process 500 can further include, responsive to detecting the triggering condition, determining an amount of power available to activate the UV light source at block 532. At block 534, the process 500 can include adjusting, based on the determined amount of power available, a parameter for activating the UV light source. In examples, the parameter can be a duration of an activation cycle during which the UV light source emits the UV light, and/or a time for initiating an activation cycle during which the UV light source emits the UV light.

Figure 9:
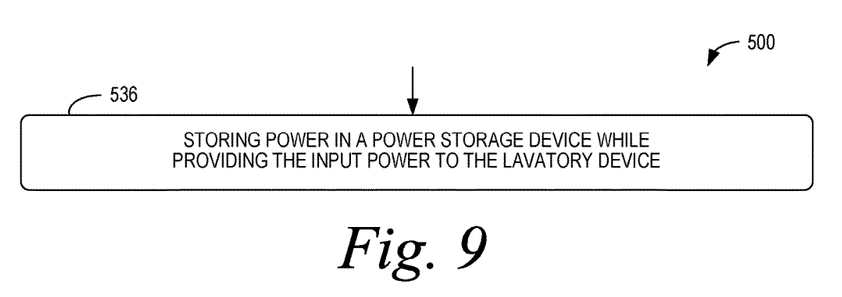
FIG. 9 illustrates a flow chart of an example process for operating a UV light source that can be used with the process shown in FIGS. 5-8.

As shown in FIG. 9, the process 500 can include storing power in a power storage device while providing the input power to the lavatory device at block 536.

Any of the blocks shown in FIGS. 5-9 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A system for disinfecting at least a portion of a lavatory in a vehicle, comprising:
    an ultraviolet (UV) light source in the lavatory and configured to emit UV light when activated;
    a switch actuatable between a first state and a second state, wherein the switch is configured to:
        while in the first state, provide an input power from a power source of the vehicle to a lavatory device in the lavatory, and
        while in the second state, provide the input power from the power source to the UV light source and cease providing the input power to the lavatory device; and
    an activation control system configured to actuate the switch between the first state and the second state to deactivate and activate the UV light source, respectively,
    wherein the input power is insufficient to simultaneously operate the lavatory device and activate the UV light source.

2. The system of claim 1, wherein the lavatory device comprises at least one device selected from the group consisting of: a water heater, a flush motor, and a vacuum blower.

3. The system of claim 1, further comprising a trigger sensor configured to detect a trigger condition and responsively generate a sensor signal indicating that the trigger condition was detected,
  wherein the activation control system is configured to:
    receive the sensor signal from the trigger sensor indicating that the trigger condition was detected,
    determine, based on the sensor signal, that one or more criteria are met, and
    responsive to a determination that the one or more criteria are met, transmit a control signal to the switch to actuate the switch from the first state to the second state.

4. The system of claim 3, wherein the trigger condition comprises at least one condition selected from the group consisting of: a door of the lavatory being opened, the door of the lavatory being closed, the lavatory being occupied, and the lavatory being unoccupied, and
  wherein the one or more criteria comprises at least one criterion selected from the group consisting of: a door of the lavatory being closed, the lavatory being unoccupied, the lavatory having been occupied a predetermined number of times since a previous activation of the UV light source, and a predetermined amount of time having passed since the previous activation of the UV light source.

5. The system of claim 1, wherein the switch comprises:
  a common terminal configured to receive the input power from the power source;
  a first terminal coupled to the lavatory device; and
  a second terminal coupled to the UV light source.

6. The system of claim 1, further comprising a power converter configured to convert the input power to a supply power,
  wherein the power converter comprises a power buffer configured to store power, and
  wherein the supply power comprises a combination of the power stored in the power buffer and the input power provided by the switch while in the second state.

7. The system of claim 6, further comprising an input coupled to the power converter and configured to receive the input power from the power source,
  wherein the switch comprises:
    a first switch configured to selectively couple the lavatory device to the input; and
    a second switch configured to selectively couple the UV light source to the power converter,
  wherein, in the first state of the switch, the first switch is closed and the second switch is open such that the lavatory device receives a first portion of the input power, the power buffer receives a second portion of the input power, and the UV light source is decoupled from the input power, and
  wherein, in the second state of the switch, the first switch is open and the second switch is closed such that the lavatory device is decoupled from the input power and the UV light source receives, via the supply power provided by the power converter, the input power.

8. The system of claim 6, further comprising a power sensor configured to determine an amount of power stored in the power buffer,
  wherein the activation control system is configured to adjust, based on the determined amount of power stored in the power buffer, a parameter for activating the UV light source during an activation cycle.

9. The system of claim 8, wherein the parameter comprises a duration of the activation cycle during which the UV light source emits the UV light.

10. The system of claim 8, wherein the parameter comprise a time for initiating the activation cycle.

11. A method of operating a ultraviolet (UV) light source, comprising:
  receiving, at a lavatory of a vehicle, an input power from a power source of the vehicle;
  providing, via a switch in a first state, the input power to a lavatory device;
  operating, using the input power while the switch is in the first state, the lavatory device;
  receiving, by the switch, a control signal from an activation control system;
  responsive to the control signal, switching the switch from the first state to a second state to: (i) provide the input power to the UV light source and (ii) cease providing the input power to the lavatory device; and
  activating, using the input power while the switch is in the second state, the UV light source to emit UV light in the lavatory.

12. The method of claim 11, wherein operating the lavatory device comprises at least one of heating water using a water heater, operating a flush motor to flush a toilet, or operating a vacuum blower to flush a toilet.

13. The method of claim 11, further comprising:
  detecting, using a trigger sensor, a trigger condition;
  transmitting, from the trigger sensor to the activation control system, a sensor signal indicating that the trigger condition was detected;
  determining, based on the sensor signal, that one more criteria are met; and
  responsive to determining that the one or more criteria are met, transmitting the control signal from the activation system to the switch.

14. The method of claim 13, wherein the trigger condition comprises at least one condition selected from the group consisting of: a door of the lavatory being opened, the door of the lavatory being closed, the lavatory being occupied, and the lavatory being unoccupied, and
  wherein the one or more criteria comprises at least one criterion selected from the group consisting of: a door of the lavatory being closed, the lavatory being unoccupied, the lavatory having been occupied a predetermined number of times since a previous activation of the UV light source, and a predetermined amount of time having passed since the previous activation of the UV light source.

15. The method of claim 13, further comprising:
  responsive to detecting the triggering condition, determining an amount of power available to activate the UV light source; and
  adjusting, based on the determined amount of power available, a parameter for activating the UV light source.

16. The method of claim 15, wherein the parameter comprises a duration of an activation cycle during which the UV light source emits the UV light.

17. The method of claim 15, wherein the parameter comprises a time for initiating an activation cycle during which the UV light source emits the UV light.

18. The method of claim 11, further comprising storing power in a power storage device while providing the input power to the lavatory device.

19. The method of claim 11, wherein the input power is insufficient to simultaneously operate the lavatory device and activate the UV light source.

20. A lavatory module configured to be installed in a vehicle, comprising:
- a plurality of walls and a door defining an interior space of the lavatory module;
- a toilet in the interior space;
- a lavatory device configured to flush the toilet;
- an ultraviolet (UV) light source configured to emit UV light in the interior space;
- an input configured to receive an input power from an electrical distribution system of the vehicle;
- a switch coupled to the input and actuatable between:
  - a first state in which the switch provides the input power to the lavatory device, and
  - a second state in which the switch provides the input power to the UV light source and ceases providing the input power to the lavatory device; and
- an activation control system configured to actuate the switch between the first state and the second state to deactivate and activate the UV light source, respectively, wherein the input power is insufficient to simultaneously power the lavatory device and activate the UV light source.

* * * * *